United States Patent [19]

Wason

[11] 4,340,583\
[45] Jul. 20, 1982

[54] HIGH FLUORIDE COMPATIBILITY DENTIFRICE ABRASIVES AND COMPOSITIONS

[75] Inventor: Satish K. Wason, Churchville, Md.

[73] Assignee: J. M. Huber Corporation, Locust, N.J.

[21] Appl. No.: 189,880

[22] Filed: Sep. 23, 1980

Related U.S. Application Data

[60] Division of Ser. No. 41,952, May 23, 1979, Continuation of Ser. No. 862,384, Dec. 20, 1977, abandoned.

[51] Int. Cl.$^3$ .......................... A61K 7/16; A61K 7/18
[52] U.S. Cl. ....................................... 424/52; 51/308; 423/335; 424/49; 424/54; 424/57
[58] Field of Search ...................... 424/52, 57; 51/308; 423/335

[56] References Cited

U.S. PATENT DOCUMENTS

| | | | |
|---|---|---|---|
| 2,399,237 | 4/1946 | Maloney | 51/308 |
| 2,649,388 | 8/1953 | Wills et al. | 51/308 |
| 2,744,001 | 5/1956 | Harman et al. | 51/308 |
| 2,820,000 | 1/1958 | Menzies | 167/93 |
| 3,122,483 | 2/1964 | Rosenthal | 424/52 |
| 3,227,618 | 1/1966 | Manahan | 424/52 |
| 3,624,199 | 11/1971 | Norfleet et al. | 424/57 |
| 3,864,470 | 2/1975 | Watson | 424/49 |
| 3,864,471 | 2/1975 | King et al. | 424/52 |
| 3,893,840 | 7/1975 | Wason | 106/288 B |
| 3,911,104 | 10/1975 | Harrison | 424/52 |
| 3,928,541 | 12/1975 | Wason | 106/288 B |
| 3,977,893 | 8/1976 | Wason | 106/288 B |
| 3,988,162 | 10/1976 | Wason | 106/288 B |
| 3,991,177 | 11/1976 | Vidra et al. | 424/50 |
| 4,015,996 | 4/1977 | Wason | 106/288 |
| 4,024,239 | 5/1977 | Pader | 424/57 |
| 4,062,658 | 12/1977 | Byrne | 51/308 |
| 4,067,746 | 1/1978 | Wason et al. | 106/288 B |
| 4,144,321 | 3/1979 | Wason | 424/52 X |
| 4,159,280 | 6/1979 | Wason | 424/52 |
| 4,244,707 | 1/1981 | Wason | 424/52 X |
| 4,280,822 | 7/1981 | Wason | 424/52 X |

FOREIGN PATENT DOCUMENTS

| | | |
|---|---|---|
| 405934 | 2/1967 | Australia . |
| 72578/74 | 2/1976 | Australia . |
| 320158 | 3/1972 | Austria . |
| 327391 | 3/1972 | Austria . |
| 327392 | 3/1972 | Austria . |
| 547129 | 3/1932 | Fed. Rep. of Germany . |
| 1054434 | 4/1959 | Fed. Rep. of Germany . |
| 2258168 | 8/1975 | France . |
| 43-11679 | 5/1968 | Japan . |
| 116438 | 3/1969 | Norway . |
| 131018 | 2/1971 | Norway . |
| 124095 | 3/1972 | Norway . |

OTHER PUBLICATIONS

Gershon et al., "Cosmetic Science and Technology", pp. 476–478, Published by Wiley-Interscience, (1983).
Jefopoulos, "Noyes Data Corporation", pp. 130–132, (1976).

*Primary Examiner*—Shep K. Rose
*Attorney, Agent, or Firm*—Robert L. Price; Harold H. Flanders

[57] ABSTRACT

Novel precipitated silicon dioxide abrasive compositions which can be incorporated into therapeutic toothpaste compositions containing both soluble fluoride salts and soluble phosphate salts are disclosed. The abrasive comprise low structure precipitated silicon dioxides which have been reacted with about 10 to 300 parts per million alkaline earth metal ion, particularly calcium. Reaction with the alkaline earth metal ion minimizes abrasive interaction with the fluoride ion source in therapeutic toothpaste. Also provided are methods for preparation of the novel silicon dioxide abrasives and resulting toothpaste formulations containing such abrasives.

8 Claims, No Drawings

HIGH FLUORIDE COMPATIBILITY DENTIFRICE ABRASIVES AND COMPOSITIONS

This is a division of application Ser. No. 041,952, filed May 23, 1979, which is a Rule 60 continuation application of Ser. No. 862,384, filed Dec. 20, 1977, now abandoned.

BACKGROUND OF THE INVENTION

1. Field of the Invention

This invention relates to improved dentifrice abrasives. More particularly, the present invention relates to novel, alkaline earth-treated, precipitated silica abrasives which are suitable for use in therapeutic toothpaste compositions containing both soluble fluoride salts as enamel solubility reducing agents and soluble phosphate salts as dental pellicle film penetration agents. The invention further relates to methods for preparing these improved precipitated silica abrasives and to toothpastes containing the improved abrasives including toothpaste embodiments which comprise both enamel solubility reducing agents (i.e. fluoride) and dental pellicle film penetration agents. Such toothpaste compositions exhibit both high fluoride compatibility and high cleaning performance.

2. The Prior Art

The function of an abrasive substance in formulations intended for use in the oral cavity is to remove various deposits, including pellicle film, from the surface of the teeth. Pellicle film is tightly adherent and often contains brown or yellow pigments and thus imparts an unsightly appearance to the teeth. An advantageous toothpaste abrasive material should maximize film removal without causing undue abrasion to the hard tooth tissue. Dental researchers are continually concerned with developing toothpaste abrasives which demonstrate satisfactory levels of cleaning and which are not unduly abrasive and damaging to the oral tissue.

In addition to abrasives, therapeutic toothpastes typically contain fluoride ion sources. The beneficial reduction in the incidence of dental caries resulting from the topical application to dental enamel surfaces of solutions containing fluoride ions is well known. Especially at solution pH's between about 4 and 8, fluoride ions are believed to interact with enamel to reduce the acid solubility of such enamel. Enamel so treated with fluoride is more resistant to the formation of denta caries. Accordingly, therapeutic toothpaste compositions are formulated to provide fluoride ion availability in brushing solutions formed in the oral cavity during use.

It has been postulated that the effectiveness of fluoride treatment in providing enamel antisolubility/anticariogenic benefits is dependent upon the amount of fluoride ion which is available for uptake by the enamel being treated. It is, of course, therefore desirable to formulate toothpaste compositions which provide maximum fluoride ion availability in brushing solutions formed therefrom. However, efforts to utilize such ionic fluoride anticariogenic agents in toothpastes suitable for home use have been unable to provide the theoretical maximum soluble fluoride because of the tendency for ionic fluoride to be inactivated and thereby rendered unavailable for enamel uptake. That is, the toothpastes lose, upon storage (at rates which increase with temperature), the capability of providing the theoretical maximum amount of soluble fluoride. For purposes of this invention, the "soluble fluoride" content of any given toothpaste composition refers to the ppm concentration of fluoride ion which is found in the supernatant sample centrifuged from 1:3 by weight slurry of the toothpaste in water (1:3=toothpaste:water).

Fluoride ion sources tend to interact with toothpaste impurities and with such toothpaste components as abrasives, buffers, etc. Such interaction diminishes the ability of the fluoride source to provide "soluble fluoride" upon use. The propensity of the toothpaste compositions herein to maintain their levels of soluble fluoride after storage is expressed hereinafter as "toothpaste fluoride compatibility". Thus, the toothpaste fluoride compatibility of a particular toothpaste composition is that percentage of the theoretical maximum amount of fluoride source that is actually measured as soluble fluoride after storage for a specified time and at a specified temperature (e.g. one week at 120° F.). Similarly, the propensity of such a dentifrice component such as the abrasive to interact with the fluoride source to diminish the measured "soluble fluoride" level from the theoretical maximum amount of fluoride sources (particularly in the presence of pellicle film penetration agents described in detail below) is expressed as "abrasive fluoride compatibility". The test procedures used herein to determine "toothpaste fluoride compatibility" values and "abrasive fluoride compatibility" values are described more fully hereinafter.

One toothpaste component which can pose special difficulties in formulating fluoride toothpastes is a precipitated silica abrasive component. Precipitated silica abrasives are desirable for use in toothpastes since they have desirably low dentin abrasion values. Certain prior art precipitated silica abrasives are generally compatible with soluble fluoride sources but have insufficiently high abrasivity to provide effective cleaning performance. Certain other prior art precipitated silica abrasives provide acceptable cleaning performance but have low abrasive fluoride compatibility as measured by the method hereinafter. It is believed that no prior art precipitated silica abrasives give both high "abrasive fluoride compatibility" as well as acceptable cleaning performance, (as indicated by standard Radioactive Dentin Abrasion values). There is thus a clear need to formulate precipitated silica abrasives which exhibit high "abrasive fluoride compatibility" as well as acceptable cleaning performance. Accordingly, it is an object of the present invention to provide precipitated silica abrasives which exhibit high "abrasive fluoride compatibility" as well as acceptable cleaning performance.

Another dentifrice component which can be especially destructive of soluble fluoride content in certain toothpaste compositions is soluble phosphate. Soluble phosphate salts, upon toothpaste use, serve to enhance the ability of fluoride ions to penetrate dental pellicle film. For this reason, soluble phosphate salts are desirably included in fluoride toothpaste compositions. However, particularly in combination with silica dental abrasives, soluble phosphate pellicle penetration agents tend to promote loss of soluble fluoride in toothpastes containing these materials and, thus, the toothpastes exhibit low toothpaste fluoride compatibility values. There is thus a clear need to formulate precipitated silica abrasives which provided high toothpaste fluoride compatibility when utilized in fluoride toothpastes containing soluble phosphate salts as pellicle film penetration agents.

There is thus a further need to provide fluoride toothpastes which can contain precipitated silica abrasives in combination with soluble phosphate salts. Accordingly, it is an object of the present invention to provide fluoride toothpaste compositions which contain soluble phosphate salts and precipitated silica abrasives and which nonetheless retain relatively high levels of soluble fluoride even after periods of storage.

It has been surprisingly discovered that the above objectives can be realized by the present invention which provides a novel precipitated silica abrasive which has been treated with an alkaline earth material, particularly calcium. By utilizing the instant dental abrasives, fluoride toothpastes—particularly those embodiments containing soluble phosphate salts—can be realized which have high toothpaste fluoride compatibility and excellent cleaning performance.

It is of course well known that therapeutic toothpaste compositions contain calcium phosphate materials as abrasives but these calcium materials are present in large amounts as described above and illustrated for example in U.S. Pat. No. 3,624,199, issued Nov. 30, 1971, Norfleet et al, and 3,864,471, issued Feb. 4, 1975, Mills et al. Toothpaste compositions are also known in the art which contain small amounts of alkaline earth metal ions, such as calcium ions, and compositions of this type are illustrated by U.S. Pat. No. 3,991,177, issued Nov. 9, 1976, Vidra et al. This patent discloses toothpaste compositions which contain a stabilizer-activator for a dextranase enzyme agent with the stabilizer-activator being a salt such as calcium chloride present in an amount of 0.001 to 0.3 weight percent. This composition can also contain therapeutic fluoride and the abrasive agent is calcium carbonate.

Other prior art which discloses toothpaste compositions containing alkaline earth metal compounds or ions include U.S. Pat. Nos. 3,095,356, issued June 25, 1963, to Moss; 3,122,483, issued Feb. 25, 1964, to Rosenthal; 3,669,221, issued June 13, 1972 to Hase; 3,782,446, issued Jan. 1, 1974, to Walter; 3,842,168, issued Oct. 15, 1974, to Colodney; and 3,689,537, issued Sept. 5, 1972, to Kuder. However, none of these prior art patents disclose therapeutic toothpaste compositions which contain as the abrasive agent a low structure precipitated silicon dioxide which contains about 10 to 300 parts per million of alkaline earth metal ion as described herein.

SUMMARY OF THE INVENTION

There is provided by the present invention a novel abrasive material for toothpaste compositions which comprises in its broadest embodiment, a precipitated silicon dioxide which is prepared from fresh water alkali metal silicate by acidulation. Such precipitated abrasives contain about 10–300 parts per million of alkaline earth metal ion, and are characterized by an RDA value of at least 40, an oil absorption value of about 70–95 ccs/100 gram, a pack density of about 0.24 to 0.55 grams per milliliter, a loss on ignition value of about 4 to 6% and a BET surface area of about 100 to 250 m$^2$/g, with an average particle size of about 5 to 15 microns. Also provided is a method for the preparation of the novel abrasives of this invention which in general comprises formation of a low structure precipitated silicon dioxide by the acidulation of certain fresh water sodium silicate solutions with a mineral acid and subsequent treatment of the resulting wet cake with the required amount of alkaline earth metal ions.

The present invention further relates to fluoride-containing toothpaste compositions which exhibit minimal loss of soluble fluoride upon storage at normal temperatures and which provide excellent cleaning performance. Such toothpaste compositions comprise the amorphous, precipitated silica abrasives of the present invention, a source of fluoride ions, a binding agent, a humectant and water. Such toothpaste compositions provide a pH of from about 4.0 to 8.0 when slurried with water in a 3:1 water/composition weight ratio.

The amorphous, precipitated silica abrasives of the present invention comprise from about 6% to 35% by weight of the toothpaste compositions.

The fluoride ion source comprises from about 0.01% to 3.0% by weight of the toothpaste compositions and can be any water-soluble material which yields fluoride ions in aqueous solution.

The binder comprises from about 0.2% to 2% of the toothpaste compositions.

The humectant comprises from about 5% to 55% by weight of the toothpaste composition. The water in the toothpastes herein comprises from about 15% to 80% by weight of composition.

DETAILED DESCRIPTION OF THE INVENTION

The present invention relates to novel, precipitated silicon dioxide dentifrice abrasives, methods for their preparation, and their incorporation into toothpastes to provide resulting compositions having excellent toothpaste fluoride compatibility values and excellent abrasivity values. The toothpaste compositions herein further essentially comprise a water-soluble fluoride ion source, a binding agent, and certain amounts of humectants and water. Each of these components as well as optional ingredients, composition use and composition preparation are described in detail as follows:

PRECIPITATED SILICA DENTAL ABRASIVE

The present invention relates to low structure precipitated silicon dioxide materials which are suitable for use as dental abrasives. Such abrasives have ultimately associated therewith about 10–300 parts per million, preferably 10–100 parts per million, of alkaline earth metal, preferably calcium, based on the amount of recoverable dry material. This dental abrasive material is characterized further by having a percent abrasive fluoride compatibility in the range of at least 90%, a RDA of at least 40, preferably from about 70 to 120, a loss on ignition (hereinafter "LOI") in the range of 4–6%, a pack density in the range of about 0.24 to 0.55 grams per milliliter, an oil absorption in the range of about 70–95 cc/100 grams and a BET surface area in the range of about 100–250 m$^2$/g with an average particle size in the range of 5–15 microns. When incorporated into a toothpaste, the dental abrasives herein provide high fluoride compatibility and excellent cleaning performance. The definition of low structure silicon dioxide materials is given in U.S. Pat. No. 3,893,840, mentioned above.

The dental abrasive materials of the present invention are precipitated silicon dioxides which are prepared by the general methods described, for example, in prior U.S. Pat. Nos. 3,893,840, issued July 8, 1975, to Wason; 3,988,162, issued Oct. 26, 1976, to Wason; and copending U.S. Application Ser. No. 703,496, filed July 8, 1976, now U.S. Pat. No. 4,067,746. Each of these patents and the application is incorporated herein by reference. Abrasives produced by such methods are subsequently treated with alkaline earth metal ions in the manner described herein. In general, the process for preparation of the silicon dioxides comprises the acidulation of an aqueous alkali metal silicate solution with a mineral acid to effect precipitation of silicon dioxide. The acid addition is continued to an acid pH and the resulting precipitated silicon dioxide is then removed such as by filtration, and washed to remove any by-product materials such as alkali metal sulfate, to provide a wet cake. The resulting wet cake is then reslurried in its own water or with additional water and thereafter is treated with the required amount of alkaline earth metal ions in the form of a soluble salt to provide the abrasive materials of this invention.

The abrasive products of the present application are to be distinguished from the precipitated silicon dioxide compositions which have been treated with alkaline earth metal ions as disclosed in my previous U.S. Application Ser. No. 723,345, filed Sept. 15, 1976, now abandoned and its continuation-in-part Ser. No. 826,901, filed Aug. 24, 1977, now U.S. Pat. No. 4,159,280, issued June 26, 1979. The silicon dioxides treated with alkaline earth metals as disclosed in copending Application Ser. No. 826,901, now U.S. Pat. No. 4,159,280, are abrasives which are useful for incorporation into toothpaste compositions so as to prevent corrosion of unlined aluminum toothpaste tubes. Such corrosion-inhibiting precipitated silicon dioxides as are described in Ser. No. 826,901, now U.S. Pat. No. 4,159,280, are silicon dioxides prepared by a so-called sulfate liquor method. In that method, an electrolyte such as alkali metal sulfate is admixed with the alkali metal silicate liquor during acidulation with mineral acid as disclosed for example in my U.S. Pat. Nos. 3,960,586 and 3,928,541. While the products of Serial No. 826,901, now U.S. Pat. No. 4,159,280, may be described as precipitated silicon dioxides having intimately admixed therewith an amount of alkaline earth metal ions which is within the range of that of the present invention, the abrasive products of the present invention have different characteristics from the silicon dioxides derived from the sulfate-liquor method. The sulfate liquor silica materials, when utilized in certain fluoride-containing toothpaste compositions, do not provide the superior fluoride compatibility values of the present invention. The superior fluoride compatibility values of the dental abrasives of this invention are achieved only with the silicon dioxides prepared from so-called fresh-water alkali metal silicate process as described herein.

The silicon dioxide abrasives of the present invention, are alkaline earth metal-treated precipitated silicon dioxides which are prepared from fresh water silicate solutions. Such a process does not make use of any electrolyte such as sodium sulfate in preparation of the untreated precipitated silicon dioxide. Further, in the products of the present invention, it has been found that the presence of alkaline earth metal ions intimately associated with the resulting silicon dioxide, must be present within a particular narrow range to provide the fluoride compatibility necessary for use in the present invention. Thus, the abrasive products of the present invention have fluoride compatibility values of at least 90%, whereas those abrasives of the prior application Ser. No. 826,901, now U.S. Pat. No. 4,159,280, generally give compatibility values of 89% or below as determined by the toothpaste fluoride compatibility tests described in this application.

It is theorized that the improved fluoride compatibility of the instant dental abrasives is based on the manner in which the silanol groups therein are attached to the surface of the silicon dioxide product. Thus, in the fresh water silicate derived silicon dioxide of the present invention, the silanol groups on the surface of the material are believed to be more available than on the sulfate liquor silicate derived silicon dioxide as disclosed in my copending U.S. Application, Ser. No. 826,901, now U.S. Pat. No. 4,159,280 filed Aug. 24, 1977. Further, the surface acidity of the fresh water silicon dioxides, due to the silanol groups, is higher than the corresponding acidity of the silicon dioxides derived from the sulfate liquor process. Because the silanol groups are different in these two materials, the intrinsic surface acidity does not respond well to calcium treatment for fluoride compatibility in the sulfate liquor products. The products of copending Ser. No. 826,901, now U.S. Pat. No. 4,159,280 also have higher abrasive values than the silicon dioxides of this application. Therefore, the instant abrasives are to be distinguished from the alkaline earth metal treated silicon dioxides disclosed in copending Ser. No. 826,901, now U.S. Pat. No. 4,159,280.

The instant precipitated silicon dioxide abrasives are preferably prepared by charging an aqueous solution of an alkali metal silicate solution, preferably a sodium silicate solution, to a reactor for acidulation. The aqueous sodium silicate solution is a fresh water solution having a sodium silicate concentration range of about 10–17 weight percent, and more preferably 12.5 to 15.5 weight percent, and a sodium silicate composition of $Na_2O.2.6\ SiO_2$ for best results. The aqueous sodium silicate solution is then raised to a temperature of about 50° to 95° C. and with continuous agitation the solution is acidulated by the addition of an aqueous solution of a mineral acid having a concentration of about 10–20 weight percent at a substantially constant pH in the range of about 8.5 to 10.5. The mineral acid is preferably sulfuric acid as sulfuric acid provides best results but as is known in the art (See U.S. Pat. Nos. 3,988,162, 3,893,840 and the copending Application Ser. No. 703,496, now U.S. Pat. No. 4,067,746 filed July 8, 1976), other acidulation agents such as nitric acid, phosphoric acid, hydrochloric acid, carbonic acid and the like can also be employed. In this regard, the disclosures of these prior patents and Ser. No. 703,496, now U.S. Pat. No. 4,067,746 are specifically incorporated herein by reference as disclosing methods for preparation of silicon dioxides of the type contemplated herein.

In the most preferred embodiment only a portion of the alkali metal silicate solution is charged to the reactor, brought to temperature under agitation, and the sulfuric acid and remainder of the alkali metal silicate solution simultaneously added to the initial silicate solution at the reaction temperature. Preferably about 8 to 12 wt. % of the metal silicate is initially charged to the reactor. The remaining portion is then added with the sulfuric acid. The time period over which the alkali metal silicate and sulfuric acid are added to the alkali metal silicate in the reactor can be predetermined and is generally based on the volume of the reactor and the difficulties in control of the temperature and agitation. After completion of the addition of the alkali metal silicate solution, the acidulation agent is continually added until the pH of the reaction slurry falls below about 6.0 and preferably to within the range of about 4.5–5.0. The resulting slurry is the precipitated silicon dioxide contained in the reaction medium.

After the pH of below 6.0 is reached, the slurry is then heated for a digestion period at a temperature of 10° to 30° C. above the reaction temperature and the reaction pH again adjusted as necessary. The resulting slurry is then filtered and washed with additional water to remove any reaction by-product such as sodium sulfate which may be contained in the silicon dioxide product. The wet cake moisture of the resulting filter cake is in the range of about 60–66% and is a low structure material. The above reaction to this point is generally the same as disclosed in my prior U.S. Pat. Nos. 3,893,840, 3,988,162 and Ser. No. 703,496, now U.S. Pat. No. 4,067,746, mentioned above, in the preparation of silicon dioxide prepared from fresh water alkali metal silicate.

In the process of the present invention, at the point of filtration and washing of the silicon dioxide wet cake, the material is then subjected to treatment with alkaline earth metal ions to produce the new abrasive products of the present invention. In accordance with the process of the present invention, the wet washed filter cake is then resluried in its own water or with the addition of fresh water at ambient temperature with agitation. While under agitation, this slurry is then treated with sufficient alkaline earth metal ions, preferably calcium ions, in the form of a salt sufficiently soluble to provide an amount of alkaline earth metal ions corresponding to about 10 to 300 parts per million, or 0.001 to 0.03 weight percent (based on the weight of the dry recoverable silicon dioxide), of alkaline earth metal ions intimately associated with the silicon dioxide.

The alkaline earth metal ion added at this point is preferably calcium ion because of its readily availability, low cost, and ease of incorporation into the silicon dioxide. The calcium ion can be incorporated into the silicon dioxide at this stage in any sufficiently water soluble form (i.e., soluble in water to the extent of at least 0.07 g/100 cc $H_2O$ at 20° C.) such as with solutions of calcium nitrate, calcium oxide, calcium hydroxide, or calcium chloride. Lime or calcium hydroxide is preferred. Also, solutions of organic salts such as calcium acetate, calcium formate, and the like can also be used. The corresponding strontium and magnesium salts of the alkaline earth class can also be used. Food grade salts should be used.

After treatment with the alkaline earth metal ion, the cake slurry is then agitated vigorously for 10–20 minutes, preferably 15 minutes, to provide the effective level of alkaline earth metal for treatment onto the surface of the silicon dioxide abrasive. The resulting product is then dried. Preferably drying is conducted in a spray dryer at an inlet temperature of 483° C. and outlet temperature of 122° C. as known in the art, and subsequently milled to the desired degree of fineness.

TOOTHPASTES

Also provided by the present invention herein are therapeutic toothpastes containing the instant novel precipitated silica abrasives. In addition to the instant abrasives, the toothpaste compositions of the present invention further comprise certain amounts of a water-soluble fluoride ion source, a binding agent, a humectant and water. Each of these additional toothpaste components as well as optional toothpaste components are described in detail as follows:

A. Abrasive

As indicated above, the instant precipitated silica abrasives are particularly suitable for incorporation into fluoride-containing therapeutic toothpaste compositions. Therapeutic toothpastes employing such abrasives provide satisfactory tooth cleaning performance and also possess excellent abrasive fluoride compatibility characteristics. The instant toothpaste compositions essentially contain from about 6% to 35%, preferably from about 10% to 20%, by weight of the instant precipitated silica abrasives.

B. Fluoride ion Source

The instant therapeutic toothpaste compositions further contain from about 0.01% to 3%, preferably from about 0.1% to 1.0%, by weight of a water-soluble, fluorine-containing material which yields fluoride ions in aqueous solutions. Such fluoride ions combine with dental enamel and thereby reduce enamel solubility in acid. Application of fluoride ions to dental enamel serves to protect teeth against decay.

A wide variety of fluoride ion-yielding materials can be employed as sources of soluble fluoride in the instant compositions. Examples of suitable fluoride ion-yielding materials are found in Briner et al; U.S. Pat. No. 3,535,421; issued October 20, 1970 and Widder et al; U.S. Pat. No. 3,678,154; issued July 18, 1972, both patents being incorporated herein by reference. Preferred fluoride ion sources for use herein include sodium fluoride (NaF), stannous fluoride ($SnF_2$), potassium fluoride (KF), potassium stannous fluoride ($SnF_2$-KF), indium fluoride ($InF_3$), zinc fluoride ($ZnF_2$), ammonium fluoride ($NH_4F$), and stannous chlorofluoride (SnClF). Sodium fluoride and stannous fluoride are particularly preferred as well as mixtures thereof.

Preferably the instant toothpaste compositions provide from about 50 ppm to 500 ppm, more preferably from about 100 to 400 ppm, of fluoride ions in the aqueous solutions which contact dental surfaces when the toothpastes of the present invention are used in the mouth. As described more fully hereinafter, such solutions are simulated by preparing 3:1 water/toothpaste slurries (by weight) of the toothpaste compositions herein and by subsequently centrifuging such slurries to obtain an aqueous supernatant. The fluoride ion concentration in such a supernatant is taken as a measure of the "soluble fluoride" provided by any given fluoride toothpaste composition.

C. Binder

A binder is essentially employed to prevent separation of the liquid and solid phases in the toothpaste compositions herein. Such binder materials are well known in the toothpaste art. The most conventionally used binders are the seaweed colloids such as Carrageenan (Irish moss or Viscarin ®) and derivatives of cellulose, such as sodium carboxymethyl cellulose and hydroxyethyl cellulose. Another type of binder which is suitable for use herein is gums such as (1) vegetable gums, e.g., guar gums and (2) fermentation products e.g., xanthan gum. The binder component generally comprises from about 0.1% to 5%, preferably 0.2% to 2% by weight of the toothpaste compositions herein. Since the natural and synthetic water dispersions of water binders are subject to microbial or mold attack, the toothpastes herein can optionally contain a relatively small amount of a preservative. Examples of preservatives typically employed are the esters of parahydroxyl benzoates.

Toothpaste binders are more fully described in Hager et al, U.S. Pat. No. 2,839,448, issued June 17, 1958; and DiGiulio, 3,862,307, issued Jan. 21, 1975. These patents are incorporated herein by reference.

D. Humectant

Another essential component of the toothpaste compositions herein is a humectant. Suitable humectant materials are also well known in the toothpaste art. The humectant serves to retain moisture and thereby to keep the toothpaste compositions from hardening upon exposure to air. Certain humectants can also impart desirable sweetness or flavor to toothpaste compositions. The humectant generally comprises from about 5% to 55%, preferably from about 20% to 36%, by weight of the toothpaste compositions herein.

Suitable humectants for use in this invention include edible polyhydric alcohols such as glycerine, sorbitol, xylitol and propylene glycol. Sorbitol is frequently employed as a 70% aqueous solution known as Sorbo ®. Mixtures of glycerine and sorbitol are especially preferred as the humectant component of the toothpaste compositions herein.

E. Water

Water is another essential element of the toothpastes of this invention. Water employed in the preparation of commercially suitable toothpastes should be deionized and free of organic impurities. Water comprises from about 15% to 80%, preferably from about 15% to 40%, by weight of the toothpaste compositions herein.

F. Optional Ingredients

In addition to the above described essential components, the toothpastes of this invention can contain a variety of optional conventional toothpaste ingredients. Such optional ingredients include (1) sudsing agents, (2) pellicle film penetration agents, (3) flavoring and sweetening agents, (4) anticalculus, antiplague agents, and (5) pigments and coloring agents.

(1) Sudsing Agent

A preferred optional ingredient is a sudsing agent. Suitable sudsing agents are those which are reasonably stable and form suds throughout a wide pH range, i.e., non-soap anionic, nonionic, cationic, zwitterionic and amphoteric organic synthetic detergents. Sudsing agents of these types are described more fully in Agricola et al; U.S. Pat. No. 3,959,458; issued May 25, 1976 and in Haefele; U.S. Pat. No. 3,937,807; issued Feb. 10, 1976. Both of these patents are incorporated herein by reference.

Anionic sudsing agents useful herein include the water-soluble salts of alkyl sulfates having from 8 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

The nonionic sudsing agents which can be used in the toothpastes of the present invention can be broadly defined as compounds produced by the condensation of alkylene oxide groups (hydrophilic in nature) with an organic hydrophobic compound which may be aliphatic or alkylaromatic in nature. Examples of suitable nonionic sudsing agents include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The zwitterionic synthetic sudsing agents useful in the toothpastes of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate.

The cationic sudsing agents useful in the toothpastes of the present invention can be broadly defined as quaternary ammonium compounds having one long alkyl chain containing from about 8 to about 18 carbon atoms such as lauryl trimethylammonium chloride; cetyl pyridinium chloride; cetyl trimethylammonium bromide; di-isobutylphenoxyethoxyethyl-dimethyobenzylammonium chloride; coconutalkyltrimethylammonium nitrite; cetyl pyridinium fluoride; etc. Especially preferred are the quaternary ammonium fluorides described in U.S. Pat. No. 3,535,421, Briner et al, issued Oct. 20, 1970, incorporated by reference hereinbefore, where said quaternary ammonium fluorides have detergent properties. The cationic sudsing agents can also act as germicides in certain of the toothpastes herein.

The amphoteric sudsing agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate.

The sudsing agent can be present in the toothpaste compositions of this invention in an amount from 0.1% to 6% by weight of the total composition.

(2) Phosphate Pellicle Penetration Agent

The toothpaste compositions of the present invention contain as a highly preferred optional component from about 5% to 12%, preferably from about 7% to 11%, by weight of a water soluble phosphate "pellicle penetration agent". Such soluble phosphate salts serve to promote transfer of fluoride ions through the naturally-occurring salivary pellicle film formed on the teeth. Fluoride-containing toothpastes which utilize the levels of phosphate salts prescribed herein demonstrate enhanced fluoride pellicle diffusion and dental enamel fluoride uptake in comparison with fluoride toothpastes which contain no such phosphate pellicle penetration agents.

While relatively high levels of soluble phosphate salts can provide fluoride pellicle penetration benefits in fluoride toothpastes, the presence of such salts can also diminish the soluble fluoride stability of such toothpastes during storage. It has been surprisingly discovered, however, that such soluble phosphate salts can be included in the silica-containing, fluoride toothpastes herein with especially beneficial fluoride compatibility results if the particular alkaline earth metal treated precipitated silica abrasives herein are employed.

Phosphate salts optionally present in the toothpaste compositions herein are water-soluble. For purposes of this invention a "water-soluble" phosphate salt is one which is soluble in water to the extent of at least 3.0 g/100 cc $H_2O$ at 20° C.

The phosphates are those phosphorus compounds in the anions of which each atom of phosphorus is surrounded by four oxygen atoms arranged at the corners of a tetrahedron. By sharing oxygen atoms between tetrahedra, chains, rings and branches polymers of interconnected $PO_4$ tetrahedra can be realized. Simple phosphates are orthophosphates. Polymeric phosphates include the polyphosphates such as the pyrophosphates and tripolyphosphates. Ring phosphates are the metaphosphates.

Examples of suitable water-soluble polyphosphates for use herein include tetrapotassium pyrophosphate, tetrasodium pyrophosphate, disodium pyrophosphate, sodium tripolyphosphate and potassium tripolyphosphate. Examples of suitable water-soluble metaphosphates include monopotassium metaphosphate, sodium trimetaphosphate, sodium hexametaphosphate, and sodium heptametaphosphate. Many of these water-soluble polyphosphates and metaphosphates are utilized in the form of hydrated salts.

The most preferred phosphate salts for use in the present invention are the simple orthophosphate salts. Orthophosphate salts are derived from tribasic orthophosphoric acid of the formula $H_3PO_4$. Water soluble sodium, potassium and ammonium salts can be utilized.

There are about ten different crystalline sodium orthophosphate salts including the various hydrates. These include, for example $NaH_2PO_4$, $NaH_2PO.H_2O$, $NaH_2PO_4.2H_2O$, $Na_2HPO_4$, $Na_2HPO_4.2H_2O$, $Na_2HPO_4.7H_2O$, $Na_2HPO_4.12H_2O$, $Na_3PO_4.6H_2O$, $Na_3PO_4.8H_2O$, and mixtures thereof. Preferred sodium orthophosphates include $NaH_2PO_4.H_2O$, $Na_2HPO_4.2H_2O$ and mixtures thereof. Especially preferred are mixtures of $NaH_2PO_4.H_2O$ and $Na_2HPO_4.2H_2O$ in a weight ratio of monosodium to disodium salt within the range of from about 1:3 to 1:5.

Potassium and ammonium orthophosphates can also be utilized as pellicle penetration agents herein. Examples of such potassium and ammonium salts include $KH_2PO_4$, $K_2HPO_4$, $K_2HPO_4.2H_2O$, $K_2HPO_4.6H_2O$, $K_3PO_4.3H_2O$, $K_3PO_4.7H_2O$, $K_3PO_4.9H_2O$, $(NH_4)H_2PO_4$, $(NH_4)_2HPO_4$, $(NH_4)_3PO_4$ and mixtures of these salts.

An especially preferred phosphate salt mixture for use in the toothpastes herein comprises a mixture of $NaH_2PO_4.H_2O$ and $K_2HPO_4.2H_2O$ in a weight ratio of sodium to potassium salt within the range of from about 1:3 to 1:5.

The soluble phosphate salts of the present invention are commercially available materials. A more detailed description of such phosphate salts useful herein can be found in Kirk & Othmer, *Encyclopedia of Chemical Technology,* Second Edition, Volume 15, Interscience Publishers, Inc. (1968), pp. 232–276, incorporated herein by reference.

Preferably the instant toothpaste compositions provide from about 0.5 mole/1000 g $H_2O$ to 2.0 moles/1000 g $H_2O$ concentrations of phosphate salts in the aqueous solutions which contact dental surfaces when the toothpastes of the present invention are used in the mouth. Again, the supernatant from 3:1 slurries of water and toothpaste are used to simulate such use solutions.

Additional pellicle film penetration agents can also optionally be added to the fluoride containing toothpastes of the present invention. Such optional ingredients further enhance the fluoride pellicle penetration benefits provided by the phosphate salts herein. Such agents include, for example, hydroxy acids and salts thereon such as citric acid, trisodium citrate, malic acid and tartaric acid. If present, such additional pellicle penetration agents comprise from about 0.2 to 5.0% by weight of the toothpaste composition.

(3) Flavoring Agents

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, acetosulpham, dihydrochalcones and sodium cyclamate. Flavoring agents are generally used in toothpastes at levels of from about 0.01% to 2% by weight and sweetening agents at levels of from about 0.05% to about 3% by weight.

(4) Antiplaque/Anticalculus Agent

Phosphorus-containing anticalculus agents and/or bis-biguanide antiplaque agents can also optionally be added to the toothpastes of this invention. Phosphorus-containing anticalculus agents such as disodium ethane-1-hydroxy-1, 1-diphosphonate and related materials are described more fully in McCune et al; U.S. Pat. No. 3,488,419, issued Jan. 6, 1970, incorporated herein by reference. Bis-biguanide antiplaque agents such as chlorhexidine (1,6-bis[$N^5$-p-chlorophenyl-$M^1$-biguanido]hexane), the soluble and insoluble salts thereof and related materials such as 1,2-bis($N^5$-p-trifluoromethylphenyl-$N^1$-biguanido)ethane are described more fully in Haefele, U.S. Pat. Nos. 3,934,002, issued Jan. 20, 1976; Haefele, 3,937,807, issued Feb. 10, 1976; Procter & Gamble, Belgian Pat. No. 843,244, published Dec. 22, 1976 and Procter & Gamble, Belgian Pat. No. 844,764, published Jan. 31, 1977. These patents are incorporated herein by reference.

If present, the optional anticalculus and/or antiplaque agents generally comprise from about 0.01% to 2.5% by weight of the toothpaste compositions herein.

(5) Pigments and Coloring Agents Misc.

A variety of other optional components well known in the art may be added to the toothpaste compositions herein to improve the usual aesthetics. These include pigments, dyes, speckles and the like. When present, these optional components generally comprise from about 0.001 to about 2% by weight of the toothpastes herein.

COMPOSITION PREPARATION

Toothpaste compositions of the present invention are prepared simply by mixing together in any order and by any conventional means the essential and optional components herein. Once prepared, the compositions herein provide a pH of from about 4.0 to 8.0, preferably 6.5 to 7.5, when said compositions are slurried with water in a 3:1 weight ratio of water to composition. Fluoride toothpastes providing pH values within the 4.0 to 8.0 range provide especially effective dental enamel antisolubility benefits compared to toothpastes with pH values outside this range. Flavoring of toothpastes within this pH range is also comparatively easy.

COMPOSITION USE

Toothpaste compositions of the present invention are used in conventional manner. The toothpaste compositions or slurries thereof are brushed onto dental surfaces and subsequently rinsed away.

During use of the toothpaste herein in conventional manner, pastes or slurries generally contact dental surfaces for at least about 30 seconds. More preferably such pastes or slurries contact dental surfaces for at least about 60 seconds.

The following examples are presented to illustrate the present invention but it is not to be considered as limited thereto. In the following examples, parts are by weight unless otherwise indicated.

EXAMPLE 1

Into a 30,000 liter stainless steel reactor jacketed for steam heating was added 1794 liters of sodium silicate solution (3.78 percent $Na_2O$, 9.53 percent $SiO_2$) of specific gravity 1.121 containing 42 grams of $Na_2O$ per liter. The reaction medium was heated to 88° C. with continuous agitation. At this point sulfuric, 10% concentration (specific gravity 1.066) and sodium silicate solution were added simultaneously to the reaction medium at the rate of 151.4 l/min. acid and 351 l/min. sodium silicate while maintaining the reaction temperature at 88° C.±1° C. These two solutions were added to the reaction medium for a predetermined length of time. The silicate addition was discontinued after 47 minutes but the acid addition was continued until the slurry pH was between 4.8–5.0. The reaction slurry was boiled at 100° C. for twenty minutes and the reaction pH was adjusted again to between 4.8–5.0. The resulting silica slurry was filtered, and washed to remove most of the reaction by-product (sodium sulfate) and the filter cake was dried and the dry product milled to the desired degree of fineness. The dry silica was subjected to various physical-chemical tests and the analysis of which are set forth hereinafter (See Table I). This example is preparation of a control product to which no alkaline earth metal is added.

EXAMPLE 2

Into a 30,000 liter stainless steel reactor jacketed for steam heating was added 1794 liters of sodium silicate solution (3.78 percent $Na_2O$, 9.53 percent $SiO_2$) of specific gravity 1.121 containing 42 grams of $Na_2O$ per liter. The reaction medium was heated to 88° C. with continuous agitation. At this point sulfuric, 10% concentration (specific gravity 1.066) and sodium silicate solution were added simultaneously to the reaction medium at the rate of 151.4 l/min. acid and 351 l/min. sodium silicate while maintaining the reaction temperature at 88° C.±1° C. These two solutions were added to the reaction medium for a predetermined length of time. The silicate addition was discontinued after 47 minutes but the acid addition was continued until the slurry pH was between 4.8–5.0. The reaction slurry was boiled at 100° C. for twenty minutes and the reaction pH was adjusted again to between 4.8–5.0. The resulting silica slurry was filtered and washed to remove most of the reaction by-product (sodium sulfate).

The washed filter cake was then reslurried without water addition at ambient temperature with agitation. While under agitation, the slurry was treated with 102 grams of Codex grade (U.S. purity food grade) hydrated lime (calcium hydroxide) to provide 25 ppm of calcium ion treatment based on the total weight of dry recoverable solid product in the slurry form. After treatment with the calcium ion, the cake slurry was agitated vigorously for 15 minutes to provide the effective level of calcium ion treatment onto the surface of the silicon dioxide abrasive. The resulting product is then spray dried at an inlet temperature of 483° C. and outlet temperature of 122° C., milled and characterized for abrasive and physical properties in the same manner as the abrasive in Example 1.

EXAMPLE 3

The method of this example was the same as in Example 2 except the rate of addition of sulfuric acid was at the rate of 162.7 liters per minute and the calcium addition was 204 grams of calcium hydroxide which provides 50 parts per million of calcium ion. The product was then characterized.

EXAMPLE 4

This example was the same as Example 2 except that the rate of addition of sulfuric acid was 166.5 liters per minute and the calcium addition comprised 408 grams of calcium hydroxide to provide 100 parts per million of calcium ion in the silicon dioxide. The product was then characterized.

EXAMPLE 5

In this example, a dentifrice silica abrasive was prepared by initially adding 1420 liters of sodium silicate solution (4.09 percent $Na_2O$, 10.31 percent $SiO_2$) of specific gravity 1.131 containing 46.3 grams of $Na_2O$ per liter to the reactor as reaction medium. The reactor was heated to 91° C. with continuous agitation. At this point sulfuric acid, 12% concentration (specific gravity 1.08) and sodium silicate solution were added simultaneously to the reaction medium at the rate of 162.7 l/min acid and 315.7 l/min sodium silicate while maintaining the reaction temperature at 91°±1° C. The silicate addition was discontinued after 47 minutes but the acid addition was continued until the slurry pH was between 4.6–4.8. The reaction slurry was boiled at 100° C. for twenty minutes and the reaction pH was adjusted again between 4.6–4.8. The resulting silica slurry was filtered and washed to remove sodium sulfate by-product.

The washed filter cake was then reslurried without water addition at ambient temperature with agitation. While under agitation the slurry was treated with 510 grams of Codex grade (U.S. purity food grade) hydrated lime (calcium hydroxide) to provide 125 ppm of calcium ion treatment based on the total weight of the dry recoverable silicon dioxide abrasive present in the slurry form. After treatment with the calcium ion, the cake slurry was agitated vigorously for 15 minutes to provide the effective level of calcium ion treatment onto the surface of the silicon dioxide abrasive. The resulting product was then spray dried at an inlet temperature of 483° C. and an outlet temperature of 122° C., milled and then characterized.

EXAMPLE 6

This example was the same as Example 5 except that 1608 liters of sodium silicate solution was initially charged to the reactor as reaction medium and the acid rate was increased to 170.3 l/min but the silicate rate was maintained at 315.7 l/min.

The washed filer cake was treated with 816 grams of calcium hydroxide to provide 200 parts per million of calcium ion treatment onto the surface of silica abrasive. The product was then characterized.

EXAMPLE 7

This example was the same as Example 2 except that the calcium ion addition was 2,040 grams of calcium hydroxide to provide 500 parts per million of calcium ions. The product was then characterized.

After preparation of the products of Examples 1 to 7 they were characterized for physical properties and the results are set forth in the following Table I.

TABLE I

| Ex. No. | % LOI* | Pack Density (g/ml.) | Oil Absorption (cc/100g.) | BET Surface*** Area ($M^2/g$) | Average Particle Size (microns)**** |
|---|---|---|---|---|---|
| 1 | 5.0 | 0.35 | 94 | 151 | 7.7 |
| 2 | 4.4 | 0.43 | 89 | 234 | 8.6 |
| 3 | 5.5 | 0.40 | 90 | 227 | 7.8 |
| 4 | 4.9 | 0.41 | 91 | 192 | 7.9 |
| 5 | 6.0 | 0.47 | 85 | 215 | 11.0 |
| 6 | 5.4 | 0.50 | 78 | 201 | 14.5 |
| 7 | 5.1 | 0.32 | 95 | 172 | 7.6 |

*Water loss when a predried silicon dioxide abrasive is heated from 105° C. and 900° C., inclusive.
**Determination of Oil Absorption, ASTM, D281-31
***J. Am. Chem. Soc. 60, 309-319 (1938)
****As measured by Coulter Counter Model TA II Several representative toothpastes of the present invention are set forth in the following examples that utilize the instant precipitated silica abrasives.

EXAMPLE 8

A toothpaste is formulated utilizing the precipitated silica abrasive of Example 2 which has the following composition:

| Component | Amount (Wt. %) |
|---|---|
| Precipitated Silica Abrasive (Example 2) | 16.0 |
| Sodium Fluoride (NaF) | 0.28 |
| Sorbitol Solution (70%) | 32.0 |
| Glycerin | 13.0 |
| Sodium Carrageenan | 0.75 |
| Monosodium Orthophosphate Monohydrate ($NaH_2PO_4 \cdot H_2O$) | 2.15 |
| Disodium Orthophosphate Dihydrate ($Na_2HPO_4 \cdot 2H_2O$) | 8.34 |
| Sodium Alkyl Sulfate Solution (28.8%) | 6.0 |
| Coconut Monoglyceride Sodium Sulfonate | 0.9 |
| Flavor | 1.22 |
| Sodium Saccharin | 0.3 |
| Color (FD&G Blue #1 Soluiton 1%) | 0.35 |
| Titanium Dioxide ($TiO_2$) | 0.5 |
| Trisodium Citrate Dihydrate ($C_6H_5Na_3O_7 \cdot 2H_2O$) | 0.25 |
| Distilled Water | q.s. |
| Total | 100.0 |

The above toothpaste composition is prepared by admixing the components thereof in the normal manner of toothpaste preparation. Preferably, the water component is first added to a suitable container to which thereafter is added with moderate agitation, in order, the pellicle film penetration agents, the flavor, the humectant and, thereafter, the remaining components.

A 3:1 weight slurry of the above freshly prepared composition with water (3:1 is water to composition) produces a pH of about 7.1.

Such a toothpaste composition provides beneficial fluoride treatment for dental tissue brushed therewith due to the high toothpaste fluoride compatibility. The toothpaste also provides good cleaning and an RDA of 100. When stored for prolonged periods of time at 80° F., such a toothpaste exhibits minimal loss of soluble fluoride.

Toothpastes providing substantially similar fluoride treatment benefits, toothpaste fluoride compatibility, and cleaning performance are realized when in the Example 8 composition, the sodium fluoride is replaced with an equivalent amount of stannous fluoride, sodium chlorofluoride, potassium fluoride, potassium stannous fluoride, indium fluoride, zinc fluoride or ammonium fluoride.

Toothpastes providing substantially similar fluoride treatment benefits and substantially similar cleaning performance are realized when, in the Example 8 composition, the phosphate salt mixture is replaced with an equivalent amount of $NaH_2PO_4$, $NaH_2PO_4 \cdot H_2O$, $NaH_2PO_4 \cdot 2H_2O$, $Na_2HPO_4$, $Na_2HPO_4 \cdot 2H_2O$, $Na_2HPO_4 \cdot 7H_2O$, $Na_3PO_4 \cdot 6H_2O$, $Na_3PO_4 \cdot 8H_2O$, $KH_2PO_4$, $K_2HPO_4$, $K_2HPO_4 \cdot 2H_2O$, $K_2HPO_4 \cdot 6H_2O$, $K_3PO_4 \cdot 3H_2O$, $K_3PO_4 \cdot 7H_2O$, $K_3PO_4 \cdot 9H_2O$, $(NH_4)H_2PO_4$, $(NH_4)_2HPO_4$, $(NH_4)_3PO_4$, other mixtures of $NaH_2PO_4 \cdot H_2O$ and $Na_2HPO_4 \cdot 2H_2O$ in monosodium to disodium weight ratios of from about 1:3 to 1:5, mixtures of $NaH_2PO_4 \cdot H_2O$ and $K_2HPO_4 \cdot 2H_2O$ in sodium to potassium salt weight ratios of from about 1:3 to 1:5, tetrapotassium pyrophosphate, tetrasodium pyrophosphate, disodium pyrophosphate, sodium tripolyphosphate, potassium tripolyphosphate, monopotassium metaphosphate, sodium trimetaphosphate, sodium hexametaphosphate or sodium heptametaphosphate; provided such compositions provide a 3:1 slurry pH of from 4.0 to 8.0.

EXAMPLE 9

A high abrasive level toothpaste is formulated utilizing the precipitated silica abrasive of Example 3 which has the following composition:

| Component | Amount (Wt. %) |
|---|---|
| Precipitated Silica Abrasive (Example 3) | 35.0 |
| Sodium Fluoride (NaF) | 0.22 |
| Glycerin | 5.0 |
| Sorbitol Solution (70%) | 20.0 |
| Carboxymethyl Cellulose (0.7 D.S.) | 0.5 |
| Magnesium Aluminum Silicate (Veegum Flakes) | 0.3 |
| Monosodium Orthophosphate Monohydrate ($NaH_2PO_4 \cdot H_2O$) | 0.3 |
| Disodium Orthophosphate Dihydrate ($Na_2HPO_4 \cdot 2H_2O$) | 0.3 |
| Sodium Alkyl Sulfate Solution (28.8%) | 2.3 |
| Coconut Monoglyceride Sodium Sulfonate | 0.7 |
| Flavor | 0.9 |
| Sodium Saccharin | 0.2 |
| Titanium Dioxide ($TiO_2$) | 0.5 |
| Speckles | 0.5 |
| Distilled Water | q.s. |
| Total | 100.0 |

Toothpastes providing substantially similar fluoride treatment benefits, toothpaste fluoride compatibility, and cleaning performance are realized when in the Example 9 composition, the precipitated silica abrasive component prepared as in Example 3 is replaced with an equivalent amount of abrasives prepared by Examples 2, 4, 5 and 6.

Toothpastes providing substantially similar fluoride treatment benefits and substantially similar cleaning performance are realized when, in the Example 9 composition, the phosphate salt mixture is replaced with an equivalent amount of $NaH_2PO_4$, $NaH_2PO_4 \cdot H_2O$, $NaH_2PO_4 \cdot 2H_2O$, $Na_2HPO_4$, $Na_2HPO_4 \cdot 2H_2O$, $Na_2HPO_4 \cdot 7H_2O$, $Na_3PO_4 \cdot 6H_2O$, $Na_3PO_4 \cdot 8H_2O$, $KH_2PO_4$, $K_2HPO_4$, $K_2HPO_4 \cdot 2H_2O$, $K_2HPO_4 \cdot 6H_2O$, $K_3PO_4 \cdot 3H_2O$, $K_3PO_4 \cdot 7H_2O$, $K_3PO_4 \cdot 9H_2O$, $(NH_4)H_2PO_4$, $(NH_4)_2HPO_4$, $(NH_4)_3PO_4$, other mixtures of $NaH_2PO_4 \cdot H_2O$ and $Na_2HPO_4 \cdot 2H_2O$ in monosodium to disodium weight ratios of from about 1:3 to 1:5, mixtures of $NaH_2PO_4 \cdot H_2O$ and $K_2HPO_4 \cdot 2H_2O$ in sodium to potassium salt weight ratios of from about 1:3 to 1:5, tetrapotassium pyrophosphate, tetrasodium pyrophosphate, disodium pyrophosphate, sodium tripolyphosphate, potassium tripolyphosphate, monopotassium metaphosphate, sodium trimetaphosphate, sodium hexametaphosphate or sodium heptametaphosphate; provided such compositions provide a 3:1 slurry pH of from 4.0 to 8.0.

EXAMPLE 10

A clear toothpaste is formulated utilizing the precipitated silica abrasive of Example 4 which has the following composition:

| Component | Amount (Wt. %) |
|---|---|
| Precipitated Silica Abrasive (Example 4) | 20.0 |
| Sodium Fluoride (NaF) | 0.24 |
| Sorbitol Solution (70%) | 57.0 |
| Glycerin | 15.0 |
| Sodium Carrageenan | 0.5 |
| Phosphoric Acid (85%) | 0.10 |
| Sodium Alkyl Sulfate Solution (28.8%) | 4.0 |
| Flavor | 1.0 |
| Sodium Saccharin | 0.2 |
| Color (FD&C Blue #1 Solution 1%) | 0.05 |
| Distilled Water | q.s. |
| Total | 100.0 |

EXAMPLE 11

A low abrasive level toothpaste is formulated utilizing the precipitated silica abrasive of Example 3 which has the following composition:

| Component | Amount (Wt. %) |
|---|---|
| Precipitated Silica Abrasive (Example 3) | 6.0 |
| Stannous Fluoride ($SnF_2$) | 0.40 |
| Sorbitol Solution (70%) | 51.0 |
| Glycerin | 25.6 |
| Sodium Carboxymethyl Cellulose (.7 DS) | 1.0 |
| Sorbitan Monoisostearate | 2.00 |
| Sodium Alkyl Sulfate Solution (28.8%) | 6.0 |
| Flavor | 1.20 |
| Sodium Saccharin | 0.28 |
| Color (FD&C Blue #1 Solution 1%) | 0.25 |
| Pyrogenic Colloidal Silica (Aerosil 200V)* | 5.00 |
| Distilled Water | q.s. |
| Total | 100.0 |

*Marketed by Degussa, Inc.

Toothpastes providing substantially similar fluoride treatment benefits, toothpaste fluoride compatibility and cleaning performance are realized when in the Example 10 composition, the precipitated silica abrasive component prepared as in Example 4 is replaced with an equivalent amount of abrasives prepared by Examples 2, 3, 5 and 6.

A toothpaste providing substantially similar fluoride treatment benefits and an improved anticalculus benefit is realized when the Example 10 composition additionally contains about 1.0% by weight of disodium ethane-1-hydroxy-1,1-diphosphonate.

TESTING AND EVALUATION

The precipitated silica abrasives herein can be used to prepare especially desirable therapeutic toothpaste compositions containing soluble phosphate pellicle film penetration agents. Such compositions provide both high abrasive fluoride compatibility and yet have good tooth cleaning performance. The following tests and evaluation serves to demonstrate the excellent fluoride compatibility provided by the precipitated silica dental abrasives herein in the toothpaste composition of the present invention. It is also shown hereinbelow that abrasives of the present invention provide higher abrasive fluoride compatibility than similarly prepared abrasives which have not been treated so as to contain the essential amounts of alkaline earth material. The excellent cleaning performance of the toothpaste compositions herein is additionally demonstrated. Finally, it is shown herein that abrasives made from a sulfate liquor acidulation process—even though containing an alkaline earth material—fail to provide the high fluoride compatibility values of the "fresh water" precipitated silica abrasives provided herein.

Abrasive Fluoride Compatibility

Precipitated silica dental abrasives can be screened for their relative compatibility with fluoride materials by means of a 24 hr. abrasive slurry test. Such a test can be used to generate data which can predict the availability of soluble fluoride in certain types of fluoride toothpastes after storage over approximately a four-week period at 80° F.

The 24 hour abrasive slurry test is used to generate fluoride compatibility values which are defined as that percentage of theoretical maximum available fluoride which is actually measured after 24 hours as soluble fluoride by the following test method. In this method (Orion Specific Ion Electrode Method) a standard sodium fluoride stock solution containing 1624 ppm of fluoride is prepared by dissolving 2.80 grams of sodium fluoride, 21.5 grams of $NaH_2PO_4$ and 83.4 grams of $Na_2HPO_4.2H_2O$ in 672.5 grams of deionized distilled water and stored in a polyethylene bottle. Thirty (30) grams of this solution is then weighed out. Seven (7) grams of the silica abrasive being tested is then dispersed into the solution and contacted for 24 hours at a temperature of about 100° F. (37.8° C.). After 24 hours, the precipitated silica abrasive/fluoride solution is centrifuged for 20 minutes at 15000 rpm or until the supernatant is clear. Then 10 ml. of the supernatant is pipetted into a plastic vial. Thereafter, 10 ml. of EDTA/THAM solution is likewise pipetted into the plastic vial. (The EDTA/THAM solution is a 0.2 molar in EDTA (ethylene diaminetetraacetic acid, disodium salt) and 0.2 molar in THAM (2-Amino-2-hydroxymethyl-1,2-propanediol) and adjusted to pH 8.0 with sodium hydroxide.) A magnetic stirring bar is added and gentle stirring is initiated. The fluoride ion concentration is determined by direct potentiometry with the Orion fluoride electrode (Model 95-09). Emf is converted to parts per million (ppm) fluoride in the supernatant by means of a logarithmic equation. The fluoride compatibility value is then calculated by expressing the measured ppm soluble fluoride as a percentage of the theoretically available soluble fluoride.

Using this method, the relative abrasive fluoride compatibility values are determined for the several abrasives prepared according to Examples 1 through 7. The results of such evaluation are set forth in the following Table II.

TABLE II

Abrasive Fluoride Compatibility

| Example No. | Calcium Treatment (ppm) | Abrasive Fluoride Compatibility |
|---|---|---|
| 1 (Control) | 0 | 76% |
| 2 | 25 | 93% |
| 3 | 50 | 94% |
| 4 | 100 | 93% |
| 5 | 125 | 91% |
| 6 | 200 | 90% |
| 7 | 500 | 88% |

The Table II data demonstrate that the precipitated silica abrasives herein containing particular amounts of an alkaline earth material provide markedly superior abrasive fluoride compatibility in comparison with that provided by an alkaline earth-free abrasive material which is otherwise similarly prepared. Thus, precipitated silica abrasives prepared as in Examples 2 through 6 should be suitable for realizing toothpastes containing fluoride and pellicle film penetration agents that demonstrate high abrasive fluoride compatibility.

Abrasive Fluoride Compatibility in Toothpastes

Preferred toothpastes herein containing precipitated silica abrasives and pellicle film penetration agents are evaluated for abrasive fluoride compatibility. The toothpastes which are prepared for evaluation have the composition of the toothpaste of Example 8 and differ only in the variation of the abrasive component.

To determine fluoride compatibility values for the toothpastes tested, a soluble fluoride determination method is used which is similar to the method described above for the determination of abrasive fluoride compatibility values. In this method, the toothpaste compositions are stored for a specified length of time in a laminate tube. Thereafter, 15.0 grams of the composition is placed in a 100 ml. beaker and then 45.0 grams of distilled water is added. The mixture then is stirred to form a slurry in which the toothpaste is uniformly dispersed. The slurry is subsequently centrifuged for 20 minutes at 15,000 rpm or until the supernatant is clear.

The supernatant is then treated as in the abrasive fluoride compatibility determination method described above. Soluble fluoride concentration is similarly measured and an abrasive fluoride compatibility value for each toothpaste is similarly calculated. The toothpaste fluoride compatibility values of the respective toothpastes evaluated are shown in Table III. The abrasives evaluated are those prepared as described in Examples 1 through 7 above and characterized in Table I above.

TABLE III

Toothpaste Fluoride Compatibility

| Abrasive (Example No.) | Calcium Treatment (ppm) | Toothpaste Fluoride Compatibility (1 wk. 80° F.) |
|---|---|---|
| 1 (Control) | 0 | 76% |
| 2 | 25 | 99% |
| 3 | 50 | 98% |
| 4 | 100 | 99% |
| 5 | 125 | 97% |
| 6 | 200 | 94% |
| 7 | 500 | 90% |

The Table III data demonstrates that the preferred toothpastes herein which utilize the instant precipitated silica abrasives provide superior abrasive fluoride compatibility values in comparison with that provided by a similar toothpaste composition containing the non-alkaline earth treated precipitated silica abrasive prepared by the method of Example 1. The data of Table III further demonstrate that the soluble fluoride availability from the fluoride ion source material is not significantly diminished upon storage when the silica abrasives of the present invention are employed in the preferred toothpastes herein.

Of course, it is to be recognized that the amount of available soluble fluoride in even the toothpaste compositions herein will decrease to some extent as a function of increasing time and temperature of storage. Thus, toothpaste fluoride compatibility values for toothpastes stored for longer periods or at more severe temperatures are generally lower than those exemplified above.

Additional abrasive fluoride compatibility data for several toothpastes demonstrating storage for longer periods and higher temperatures are shown in Table IV.

TABLE IV

Toothpaste Fluoride Compatability (High Temperature/Prolonged Storage)

| Abrasive (Example No.) | Calcium Treatment (ppm) | Toothpaste Flouride Compatibility | | | |
|---|---|---|---|---|---|
| | | 1 week 80° F. | 1 week 120° F. | 4 month 80° F. | 5 month 80° F. |
| 1 | 0 | 76% | 64% | — | 64% |
| 2 | 25 | 99% | 97% | 91% | — |
| 3 | 50 | 98% | 96% | 91% | — |
| 4 | 100 | 99% | 95% | 91% | — |
| 5 | 125 | 97% | 92% | — | — |
| 6 | 200 | 94% | 90% | — | — |
| 7 | 500 | 90% | 86% | — | 89% |

The Table IV data demonstrate that the preferred toothpastes herein maintain their relatively high fluoride abrasive compatibility levels even under prolonged storage or under severe storage conditions.

Cleaning Performance

The dental cleaning ability of the silica abrasives herein can be estimated by means of Radioactive Dentin Abrasion (RDA) testing. RDA values can be used to estimate the relative cleaning performance of various abrasives for any given type of dentifrice abrasive. Thus, for precipitated silica abrasives, an RDA value (measured by the method provided below) of at least 40, preferably between 70 and 120, is needed to insure that the abrasive has sufficient abrasivity to be an effective dentifrice cleaner. Prior art precipitated silica abrasives which do exhibit high toothpaste fluoride compatibility generally are poor cleaners for oral hygiene purposes as evidenced by low RDA values. The alkaline earth treated abrasives, however, provide both effective tooth cleaning and high fluoride compatibility.

Several commercial precipitated silica abrasives which demonstrate relatively high toothpaste fluoride compatibility as measured herein are selected for evaluation for RDA values. Testing is conducted within a standard toothpaste matrix having the composition of the toothpaste of Example 8, which differs only in the variation of the abrasive component.

The method which is employed for determining the RDA values for toothpastes that are tabulated in Table V is described below. This test method is described more fully in the *Journal of Dental Research*, July-August, 1976, by Hefferren, pp. 563-573. The specific steps for determining RDA values are set forth as follows:

A. Selection and preparation of teeth

Sound, single-rooted permanent teeth that are caries-free and vital at extraction are selected. Teeth are then scraped clean with a scalpel. The crown and root tip of each tooth are removed using an abrasive disc so as to prepare a dentin sample 14 mm long and at least 2 mm wide at the narrower end. Cut pieces of root (dentin chips) or, alternatively, an additional tooth, are also prepared to be later used in determining a correction factor for self-absorption of radiation.

B. Irradiation of dentin

The prepared roots and dentin chips described in Step A are exposed to a neutron flux of $2 \times 10^{12}$ neutrons/cm$^2$ for three hours.

C. Mounting of roots

After irradiation, the irradiated roots are embedded in a mount of cold-curing dental methacrylate resin and mounted onto a cross-brushing machine. Toothbrushes used throughout the test are 50-Tuft, medium, flat, "Pepsodent" toothbrushes.

D. Preconditioning the dentin surfaces

Prior to initial test run, the freshly mounted, irradiated roots are brushed with a reference slurry (10 g calcium pyrophosphate + 50 ml of a 0.5% CMC-10% glycerine solution) for 6,000 brush strokes. At the beginning of each subsequent day's test run, the roots are brushed for 1,000 strokes.

E. Test run

After preconditioning, the dentin samples are then conditioned with the reference slurry (same slurry as in Step D) for 1,500 brush strokes at the beginning, during and end of each test run. The test run consists of brushing dentin samples for 1,500 brush strokes with a slurry of test product (25 g dentifrice + 40 ml deionized of distilled water).

F. Preparation of correction factors

The correction factors are prepared by dissolving the dentin chips or, alternatively, an additional tooth, from Step B in 5 ml. conc. HCl brought to a volume of 250 ml. with distilled water. One ml. of this solution is added to test pastes and reference slurries which are prepared similarly to those in Step E, and then neutralized with 0.1 N NaOH.

Radioactive Tracer Counting

The radioactivity of the slurry samples (1.0 ml.) is determined with an Intertechnique SL-30 liquid scintillation counter. Alternate counting procedure: 3 ml. aliquots of each slurry are transferred to stainless steel, flat-bottom 1 inch × 5/16 inch planchets and counted using Nuclear Chicago Geiger Counting System.

Calculations

The radioactive dentin abrasion value (RDA) for a particular paste will be the ratio of the average corrected counts for that paste to the average count for the reference multiplied by 100. The reference abrasive is given an arbitrary dentin abrasion value of 100 units.

The results of such RDA value determination are set forth in the following Table V.

TABLE V

| Abrasive | RDA | Toothpaste Fluoride Compatibility One Week (80° F.) |
|---|---|---|
| A. (Example No.) | | |
| 1. Control | 75 ± 7 | 76% |
| 2. | 80 ± 21 | 99% |
| 3. | 67 ± 8 | 98% |
| 4. | 80 ± 1 | 99% |
| 5. | 103 ± 5 | 97% |

TABLE V-continued

| Abrasive | RDA | Toothpaste Fluoride Compatibility One Week (80° F.) |
|---|---|---|
| 6. | 111 ± 5 | 94% |
| 7. | 56 ± 4 | 90% |
| B. Commercial Precipitated Silica Products | | |
| 8. Sident 3 [1] | 14 ± 2 | 92% |
| 9. Neosyl [2] | 25 ± 2 | 78% |
| 10. QUSO G-30 [3] | 22 ± 2 | 87% |
| 11. Neosyl ET [4] | 26 ± 4 | 84% |

[1] A precipitated silica marketed by Degussa, Inc. (N.Y.C.).
[2] A precipitated silica marketed by Joseph Crosfield & Sons, Ltd. (London, England).
[3] A precipitated silica marketed by Philadelphia Quartz Co. (Valley Forge, Pa.).
[4] A precipitated silica marketed by Joseph Crosfield & Sons, Ltd.

The Table V data demonstrates that commercial precipitated silica abrasives may well demonstrate high abrasive fluoride compatibility but are not sufficiently abrasive so as to be useful as dentifrice abrasives. Surprisingly, the instant novel precipitated silica abrasives provide outstanding abrasive fluoride compatibiity yet simultaneously provide excellent RDA abrasivity values, which values can be used as an indicator of relative dental cleaning performance.

"Fresh Water" versus "Sulfate Liquor" Abrasives

As indicated hereinabove the abrasive products of the present invention are related to but distinctly different from the calcium treated silicas of copending application Ser. No. 826,901, now U.S. Pat. No. 4,159,280. To demonstrate such a difference, the following evaluation is made to compare the fluoride compatibility of the products of application Ser. No. 826,901, now U.S. Pat. No. 4,159,280, with that of the abrasive products of this invention. The "sulfate liquor" silicon dioxide materials tested are prepared in accordance with the process disclosed in Ser. No. 826,901, now U.S. Pat. No. 4,159,280, and U.S. Pat. No. 3,960,586, issued June 1, 1976, by the following procedure:

Dry sodium sulfate was added to 10.0 gallons of water in a 200 gallon reactor so that the sodium sulfate concentration in the reaction medium was 10%. The pH of the reaction medium was then adjusted to 9.0 by the addition of sodium silicate. The reaction temperature was 65° C. (150° F.). The sodium silicate solution had an SiO$_2$/Na$_2$O mole ratio of 2.5 and a concentration of 2.0 pounds per gallon. Sodium silicate was added to the reaction medium for 4 minutes. At this point the sodium silicate addition was stopped and sulfuric acid of 11.4% of concentration was added to the reaction medium until the pH of 9.0 was reached. At this point the sodium silicate solution and the sulfuric acid solution were added simultaneously for a period of 35 minutes. At the end of the 35 minute period of silicate addition, the silicate was discontinued and the acid addition was continued until a slurry pH of 5.5 was obtained. The batch was digested at 77° C. for 20 minutes and the resulting wet cake recovered and washed.

The wet cake was then treated in the manner described for Example 2 of this application, divided into six separate portions and treated respectively with 50, 100, 200, 400 and 800 parts per million of calcium from aqueous solutions of calcium hydroxide. Each wet cake was then dried and processed as described for Example 2 and characterized in the following Table VI where the first abrasive is a control in which no calcium was added. Table VI sets forth the results of such evaluation.

TABLE VI

| "Sulfate Liquor" Abrasive | Ca Addition (ppm) | Abrasive Fluoride Compatibility* |
|---|---|---|
| A | 0 (control) | 88 |
| B | 50 | 89 |
| C | 100 | 88 |
| D | 200 | 88 |
| E | 400 | 86 |
| F | 800 | 82 |

*Determined by test described for Table II.

As can be seen from the Table VI data, the calcium treated "sulfate liquor" abrasives of copeding application Ser. No. 826,901, now U.S. Pat. No. 4,159,280, provide abrasive fluoride compatibility values which are generally lower than those provided by the "fresh water" silica abrasives of the present invention (See Table II.). Furthermore, the addition of an alkaline earth metal to abrasives made by the "sulfate liquor" method does not result in a dramatic improvement in abrasive fluoride compatibility. Conversely, as can be seen from a comparison of Table II, the addition of equivalent amounts of alkaline earth metal to the silica abrasives herein made by the "fresh water" method does result in dramatic improvements in abrasive fluoride compatibility.

What is claimed is:

1. A toothpaste composition, comprising:
   A. from about 6% to 35% by weight of a precipitated silica abrasive material which is a precipitated amorphous silicon dioxide prepared from fresh water alkali metal silicate by acidulation, which has been intimately reacted with a solution of an hydroxide or an oxide or a salt or a sufficiently water soluble form of an alkaline earth metal so as to have present about 10–300 parts per million of alkaline earth metal ions in said amorphous silicon dioxide, said amorphous silicon dioxide exhibiting a Radio-active Dentin Abrasion value of at least 40, an average particle size of from about 5 to 15 microns in diameter, a pack density of about 0.24 to 0.55 grams per milliliter, an oil absorption of about 70–95 ccs/100 grams, a BET surface area of about 100–250 m$^2$/g, and a percent loss on ignition of about 4–6%;
   B. from about 0.01% to 3.0% by weight of a water-soluble, fluorine containing material which yields fluoride ions in aqueous solution;
   C. from about 3% to 55% by weight of a humectant;
   D. from about 0.2% to 2.0% by weight of a binding agent; and
   E. from about 15% to 80% by weight of water;
said composition providing a pH of from about 4 to 8 when slurried with water in a 3:1 water/composition weight ratio.

2. A toothpaste composition in accordance with claim 1, which composition additionally contains from about 5% to 12% by weight of a water-soluble phosphate pellicle film penetration agent selected from the group consisting of orthophosphate salts, pyrophosphate salts, tripolyphosphate salts and metaphosphate salts.

3. A toothpaste composition in accordance with claim 2 wherein:
   A. the precipitated silica abrasive comprises from about 10% to 20% by weight of the composition;
   B. the fluorine-containing material comprises from about 0.1% to 1.0% by weight of the composition;
   C. the humectant comprises from about 20% to 35% by weight of the composition;
   D. the water component comprises from about 15% to 40%; and
   E. the pH provided by a 3:1 water/composition slurry ranges from about 6.5 to 7.5.

4. A composition in accordance with claim 3 which composition additionally contains from about 0.1% to 6% by weight of the composition of a sudsing agent; and wherein
   A. the fluorine-containing material is selected from the group consisting of sodium fluoride and stannous fluoride;
   B. the phosphate pellicle film penetration agent is an orthophosphate salt; and
   C. the humectant is selected from the group consisting of glycerine, sorbitol, xylitol and mixtures thereof.

5. A composition in accordance with claim 4 wherein
   A. the fluorine-containing material is sodium fluoride; and
   B. the sudsing agent is selected from the grop consisting of:
      1. the water-soluble salts of alkyl sulfates having from about 8 to 18 carbon atoms in the alkyl radical,
      2. the water-soluble salts of sulfonated monoglycerides of fatty acids having from about 8 to 18 carbon atoms in the fatty acid moiety; and
      3. mixtures thereof.

6. A composition in accordance with claim 3 wherein the binding agent is carrageenan.

7. A composition in accordance with claim 4 which composition additionally contains from about 0.2% to 5% by weight of the toothpaste composition of a second pellicle film penetration agent selected from the group consisting of citric acid, trisodium citrate, malic acid and tartaric acid; and wherein
   A. the fluorine-containing material is sodium fluoride; and
   B. the phosphate pellicle film penetration agent is a mixture of sodium dihydrogen phosphate monohydrate and disodium hydrogen phosphate dihydrate in monosodium to disodium weight ratio of about 1:3 to 1:5.

8. A toothpaste composition in accordance with claim 3 which contains an additional component selected from the group consisting of
   A. from about 0.01% to 2% by weight of a flavoring agent;
   B. from about 0.05% to 3% by weight of a sweetening agent;
   C. from about 0.01% to 2.5% by weight of an anticalculus agent which is disodium ethane-1 hydroxy-1,10diphosphonate;
   D. from about 0.01% to 2.5% by weight of a bis-biguanide antiplaque agent; and
   E. mixtures of these additional toothpaste composition components.

* * * * *

UNITED STATES PATENT AND TRADEMARK OFFICE
CERTIFICATE OF CORRECTION

PATENT NO. : 4,340,583

DATED : July 20, 1982

INVENTOR(S) : Satish K. Wason

It is certified that error appears in the above—identified patent and that said Letters Patent is hereby corrected as shown below:

In Abstract, fifth line, "abrasive" should be -- abrasives --.

Column 1, line 48, "denta" should be -- dental --.

Column 2, line 63, "provided" should be -- provide --.

Column 6, line 64, "4.5-5.0" should be -- 4.6-5.0 --.

Column 14, line 23, following "reaction", the comma "," should be omitted.

Column 15, Table I, in fourth columnar heading, following "Absorption", two asterisks -- ** -- should be inserted.

Column 16, line 64, "$K_3PC_4 \cdot 9H_2O$" should be -- $K_3PO_4 \cdot 9H_2O$ --.

Column 20, about line 21, in Table IV heading, "Compatability" should be -- Compatibility --.

UNITED STATES PATENT AND TRADEMARK OFFICE
CERTIFICATE OF CORRECTION

PATENT NO. : 4,340,583

DATED : July 20, 1982

INVENTOR(S) : Satish K. Wason

It is certified that error appears in the above-identified patent and that said Letters Patent is hereby corrected as shown below:

Column 23, line 15, "copeding" should be --copending--.
Column 24, line 28, "grop" should be --group--.

Signed and Sealed this

Second Day of November 1982

[SEAL]

Attest:

GERALD J. MOSSINGHOFF

Attesting Officer

Commissioner of Patents and Trademarks